United States Patent [19]

Gitlitz

[11] 4,010,276
[45] Mar. 1, 1977

[54] CERTAIN TRIORGANOTIN COMPOUNDS USED TO COMBAT MITES

[75] Inventor: Melvin H. Gitlitz, Edison, N.J.

[73] Assignee: M & T Chemicals Inc., Greenwich, Conn.

[22] Filed: June 16, 1975

[21] Appl. No.: 587,034

Related U.S. Application Data

[60] Division of Ser. No. 487,053, July 10, 1974, Pat. No. 3,923,998, which is a continuation-in-part of Ser. No. 311,509, Dec. 4, 1972, abandoned.

[52] U.S. Cl. .............................................. 424/288
[51] Int. Cl.$^2$ ........................................... A01N 9/00
[58] Field of Search ................................... 424/288

[56] References Cited

UNITED STATES PATENTS

| | | | |
|---|---|---|---|
| 3,264,177 | 8/1966 | Kenaga | 424/288 |
| 3,445,575 | 5/1969 | Taylor | 424/288 |
| 3,552,945 | 1/1971 | Plonsker et al. | 71/97 |
| 3,632,769 | 1/1972 | Pellegrini et al. | 424/288 |
| 3,702,360 | 11/1972 | Graham | 424/288 |
| 3,923,998 | 12/1975 | Gitlitz | 424/288 |

OTHER PUBLICATIONS

Chemical Abstracts 72:100842f (1970).

Primary Examiner—Leonard Schenkman
Attorney, Agent, or Firm—Robert P. Auber; Kenneth G. Wheeless; Robert Spector

[57] ABSTRACT

Dicyclohexylphenyltin compounds of the general formulae

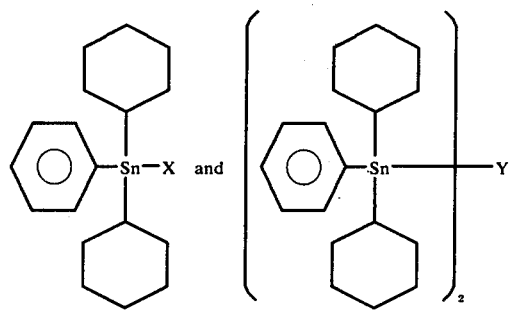

effectively combat fungi and mites when applied to these organisms or to objects, particularly plants, that are susceptible to attack by the organisms, yet are less phytotoxic than the corresponding triphenyltin compounds. In the foregoing formulae X is a chlorine, bromine, fluorine, hydroxyl, carboxylate, phenoxy, alkoxy (-OR$^1$) or mercaptide (-SR$^2$) radical wherein R$^1$ represents an alkyl radical containing between 1 and 12 carbon atoms, inclusive, R$^2$ is a radical selected from the same group as R$^1$ or an aryl radical and Y is an oxygen, sulfur, or a sulfate radical.

1 Claim, No Drawings

CERTAIN TRIORGANOTIN COMPOUNDS USED TO COMBAT MITES

This is a divisional of application Ser. No. 487,053 filed July 10, 1974 now U.S. Pat. No. 3,923,998 which is a continuation-in-part of application Ser. No. 311,509, filed Dec. 4, 1972 now abandoned.

This invention relates to a method for selectively controlling fungi and mites using a specific class of unsymmetrically substituted triorganotin compounds. The organisms against which this class of compounds is effective are responsible for a considerable portion of the annual damage to agricultural crops, particularly tomatoes, apples, and rice. Over the years fungi and mites have developed a resistance to many chemicals which had previously been effective in combating them. The development of resistant strains has mandated a search for new miticides and fungicides. Some triorganotin compounds effectively control these pests; however, many of these compounds, particularly those wherein the hydrocarbon radicals bonded to the tin atom contain 1 to 4 carbon atoms or a phenyl radical, are relatively non-selective when applied to desirable plants, in that while the organism attacking the plant may be controlled, the plant itself is killed or severely damaged.

SUMMARY OF THE INVENTION

It has now been found that liquid or solid formulations containing as the toxicant a dicyclohexylphenyltin compound of the general formula effectively control fungi and mites. Unlike the corresponding triphenyltin derivatives, there is little, if any, damage to plants which have been treated with efficacious amounts of the present compounds. In the foregoing formulae, X represents a radical selected from the group consisting of chlorine, bromine, fluorine, hydroxyl, carboxylate, phenoxy, alkoxy ($-OR^1$), and mercaptide ($-SR^2$), wherein $R^1$ represents an alkyl radical containing between 1 and 12 carbon atoms, inclusive, $R^2$ is a radical selected from the same group as $R^1$ or an aryl radical and Y is an oxygen, sulfur, or sulfate radical.

DETAILED DESCRIPTION OF THE INVENTION

All of the present dicyclohexylphenyltin compounds can be obtained from the corresponding bromide, either directly or by first reacting the bromide to form the hydroxide or oxide. Dicyclohexylphenyltin bromide is prepared by reacting dicyclohexyldiphenyltin with bromine. The ability of bromine to selectively cleave a hydrocarbon radical from a tetraorganotin compound has been disclosed in the chemical literature for the preparation of other triorganotin compounds. Preferably dicyclohexyldiphenyltin is dissolved in a suitable solvent or mixture of solvents to which a solution of bromine is gradually added. Suitable solvents include alcohols containing between 1 and 8 carbon atoms and liquid halogenated hydrocarbons. Any compound which is a liquid at the reaction temperature and does not react with bromine or the tetraorganotin compound is suitable for this purpose. The reaction mixture is maintained below ambient temperature, preferably between $-30°$ and $25°$ C., during addition of the bromine to control the degree of hydrocarbon radical cleavage, thereby maximizing the yield of dicyclohexylphenyltin bromide. The reaction is believed to proceed in accordance with the following equation:

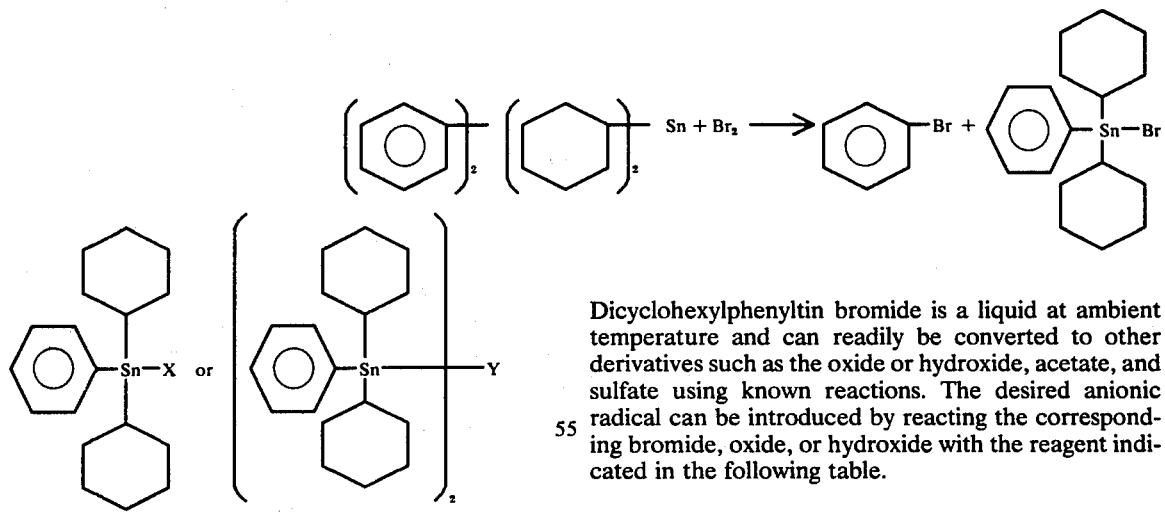

Dicyclohexylphenyltin bromide is a liquid at ambient temperature and can readily be converted to other derivatives such as the oxide or hydroxide, acetate, and sulfate using known reactions. The desired anionic radical can be introduced by reacting the corresponding bromide, oxide, or hydroxide with the reagent indicated in the following table.

| ORGANOTIN DERIVATIVE + | REAGENT ⟶ | DESIRED PRODUCT |
|---|---|---|
| Bromide | Carboxylic acid + acid acceptor, e.g. pyridine | carboxylate, e.g. acetate |
| " | alkali metal salt of carboxylic acid | " |
| " | aqueous solution of | hydroxide or |

-continued

| ORGANOTIN DERIVATIVE + | REAGENT | → DESIRED PRODUCT |
|---|---|---|
| | alkali metal hydroxide | oxide |
| " | alkali metal alkoxide or alcohol + acid acceptor | alkoxide |
| " | alkali metal phenoxide or phenol + acid acceptor | phenoxide |
| " | potassium fluoride or hydrofluoric acid | fluoride |
| " | alkali metal sulfide | sulfide |
| " | alkali metal sulfate | sulfate |
| " | mercaptan + acid acceptor | mercaptide |
| Oxide (or hydroxide) | carboxylic acid or anhydride | carboxylate |
| " | alcohol (or phenol) | alkoxide (or phenoxide) |
| " | hydrofluoric acid | fluoride |
| " | dilute (10–25 weight %) aqueous sulfuric acid | sulfate |
| " | hydrogen sulfide | sulfide |
| " | alkyl or aryl mercaptan | mercaptide |
| " | aqueous hydrochloric acid | chloride |

The reaction conditions such as preferred solvents, temperatures and reaction times for preparing the derivatives summarized in the preceding table are known in the art and, therefore, do not require a detailed description in the present specification. A comprehensive treatment of this subject matter is contained in an article by R. K. Ingham et al. that appeared in the October, 1960 issue of CHEMICAL REVIEWS (p.p. 459–539).

It is known that an equilibrium exists between a triorganotin hydroxide and the corresponding bis(triorganotin) oxide, which differ only by the presence or absence of a mole of water for every two moles of compound. It is often difficult to determine which of the two compounds is present. The compound which predominates in a given instance is often determined by the conditions under which the compound is stored, particularly the amount of water present in the environment. The hydroxide is readily converted to the oxide by dehydration under reduced pressure.

The dicyclohexylphenyltin compounds are liquid or solid materials at ambient temperature, depending upon the type of substituent represented by X or Y.

Efficacious amounts of dicyclohexylphenyltin compounds can be applied to plants for the purpose of combating undesirable mites and fungi without significantly damaging the plants. A single application of these compounds can provide residual and extended control of fungi and mites for a considerable period of time, the duration of which is dependent to some extent upon mechanical and biological influences, including weather, but is sometimes as long as several months. Triphenyltin compounds, particularly the oxide, control many types of fungi, however these compounds do considerable damage to certain types of desirable plants which limits their usefulness.

Tricyclohexyltin compounds are effective miticides but cannot control many types of fungi. The present dicyclohexylphenyltin compounds offer the advantages of both triphenyl- and tricyclohexyltin compounds together with a reduced level of toxicity to both plants and warm blooded animals relative to the aforementioned prior art compounds. In preparing compositions for application to plants, the tin compound is often augmented or modified by combining it with one or more commonly employed pesticide additives or adjuvants including organic solvents, water or other liquid carriers, surface active dispersing agents or particulate and finely comminuted or divided solid carriers. Depending upon the concentration of the tin compound in these compositions, they can be employed either directly to control the organisms or as concentrates which are subsequently diluted with inert liquids or solids to produce the ultimate treating compositions. In compositions to be employed as concentrates, the dicyclohexylphenyltin compound can be present at concentrations of from about 5 to about 98% by weight. Baits, attractants and the like can also be included for combating mites. Other biologically active agents that are chemically compatible with the present tin compounds can also be added. Depending on the desired method of application the final formulation is a liquid or a solid.

The optimum concentration of organotin compounds in a formulation suitable for applying an effective amount of the organotin compound to the organism directly or to its habitat or food will vary, and is primarily dependent upon the susceptibility of a particular organism to the organotin compound and whether the formulation is to be applied as a liquid spray or a solid dust. The effective level in sprays, which are usually applied to plants in an amount sufficient to completely saturate the upper surface of the leaves, is between 4 and 500 parts by weight per million of total formulation. The final spray is usually prepared near the location where it is to be applied by combining a concentrate in the form of a wettable powder or liquid with a sufficient amount of water or other liquid to achieve the desired concentration level. The concentrates should be readily soluble or dispersible in the liquid diluent. A surfactant may be required to facilitate dispersing of the concentrate in the liquid diluent. Suitable diluents other than water include methanol, ethanol, isopropanol, methyl ethyl ketone, acetone, methylene chloride, chlorobenzene, toluene, xylene, and petroleum distillates. Among the preferred petroleum distillates are those boiling almost entirely under 400° F. at atmospheric pressure and having a flash point above about 80° F.

Alternatively, the dicyclohexylphenyltin compound can be dissolved in a mixture of a suitable water-immiscible organic liquid and surface active agent to produce emulsifiable concentrates which may be further diluted with water to form spray mixtures in the form of oil-in-water emulsions. In such compositions, the carrier comprises an aqueous emulsion, i.e., a mixture of water-immiscible solvent, emulsifying agent and water. Preferred dispersing agents for these compositions are oil soluble and include the condensation products of alkylene oxides with phenols and organic and inorganic acids, polyoxyethylene derivatives of sorbitan esters, alkylarylsulfonates, complex ether alcohols, mahogany soaps and the like. Suitable organic liquids to be employed in the compositions include petroleum distillates, hexanol, liquid halohydrocarbons and synthetic organic oils. The surface active dispersing agents are usually employed in the liquid dispersions and aqueous emulsions in the amount of from about 1 to about 20 percent by weight of the combined weight of the dispersing agent and the active toxicant.

In the preparation of dust compositions, the dicyclohexylphenyltin compound can be blended with many commonly employed finely divided solids, such as fuller's earth, attapulgite, bentonite, pyrophyllite, vermiculite, diamtomaceous earth, talc, chalk, gypsum, wood flour, and the like. In such operations, the finely divided carrier is ground or mixed with the toxicant or wetted with a dispersion of the toxicant in a volatile liquid. Depending upon the proportions of ingredients, these compositions can be employed as concentrates and subsequently diluted with additional solid of the types indicated hereinbefore, to obtain the desired amount of active ingredient in a comminuted composition adapted for the control of pests. This type of composition requires higher levels of organotin toxicant than a spray. Concentrations of between 0.1 and 10%, based on the weight of the total formulation is usually required to effectively control fungi and mites.

When operating in accordance with the present invention, a spray or dust composition containing the compound can be applied directly to the undesirable organism when mites are being controlled, or to their habitat or food in any convenient fashion, i.e., by means of hand dusters or sprayers or by simple mixing with the food to be ingested by the mites. Application to the foliage of plants to combat fungi is conveniently carried out using power dusters, boom sprayers and spray dusters. When employed in this manner the compositions should not contain any significant amounts of phytotoxic diluents. In large scale operations, dusts or dilute sprays are often applied from an aircraft.

The following examples represent preferred embodiments of the present invention and should not be interpreted as limiting the scope thereof.

EXAMPLE 1

This example discloses a method for preparing dicyclohexylphenyltin bromide.

A solution containing 171.9 g. (0.5 mole) of diphenyltin dichloride and 500 c.c. of toluene was added gradually over 1.25 hours to 1 liter of mixture containing 1.5 moles of cyclohexyl magnesium chloride and tetrahydrofuran as the diluent. The reaction vessel was equipped with a mechanically driven agitator, water-cooled reflux condenser, addition funnel, thermometer and nitrogen inlet. The temperature of the reaction mixture gradually increased to 61° C. during the addition, following which a 250 c.c. portion of toluene was added.

After the reaction mixture had been heated at the boiling point for 1.5 hours, then cooled to ambient temperature, a solution containing 55 g. of citric acid and 400 c.c. of water was added. The organic liquid phase was separated and dried by combining it with a quantity of anhydrous magnesium sulfate, after which the liquid phase was filtered and concentrated under reduced pressure until it appeared turbid. The addition of 250 c.c. of methanol yielded a precipitate which was isolated and washed with methanol. The dried solid weighed 207.5 g. (94.5% of theoretical yield) and was found to contain 27.27% by weight of tin. The calculated tin content of dicyclohexyldiphenyltin is 27.02%.

A solution containing 16.0 g. (0.1 mole) bromine, 50 c.c. methanol, and 50 c.c. chloroform was added dropwise to a solution containing 43.9 g. (0.1 mole) of dicyclohexyldiphenyltin, 50 c.c. methanol and 110 c.c. chloroform. The addition required 105 minutes, during which time the temperature of the reaction mixture was maintained at 0° C. Each drop of bromine was added only after the color imparted by addition of the preceding drop had disappeared. Following completion of the addition the resultant clear solution was concentrated under reduced pressure to yield a colorless liquid weighing 51.3 g. and exhibiting a refractive index ($\eta_D^{25}$) of 1.5826. 4.0 grams of unreacted dicyclohexyldiphenyltin precipitated following the addition of 150 c.c. of methanol to the crude product and was isolated by filtration. The methanol was removed from the liquid phase under reduced pressure. The liquid was then treated with anhydrous ammonia to precipitate dicyclohexyltin dibromide as the solid ammonia complex, which was isolated by filtration. The filtrate was concentrated under reduced pressure to yield 22.2 g. of a liquid which upon analysis by vapor phase chromatography was found to contain 96% by weight of dicyclohexylphenyltin bromide.

EXAMPLE 2

Preparation of Dicyclohexylphenyltin Hydroxide

Dicyclohexylphenyltin hydroxide was prepared by adding a solution containing 3.0 g. (0.075 mole) sodium hydroxide and 25 c.c. water to a solution containing 20.7 g. (0.047 mole) dicyclohexylphenyltin bromide and 205 c.c. methanol. Following completion of the addition the resultant mixture was heated at the boiling point for one hour, then allowed to cool to ambient temperature with agitation. A 200 c.c. portion of water was added to the resultant mixture, which contained a white solid precipitate. The solid material was isolated, washed with deionized water until free of bromide and then dried in a circulating air oven. The dried solid weighed 16.7 g. (93.8% of theoretical yield) and was found to contain 31.65% by weight of tin. The calculated tin content for dicyclohexylphenyltin hydroxide is 31.31%.

BIOLOGICAL ACTIVITY OF DICYCLOHEXYLPHENYLTIN HYDROXIDE

1. Preparation of Spray Formulations

Dicyclohexylphenyltin hydroxide and the triorganotin compounds employed as controls were formulated into sprayable compositions by dissolving or dispersing the compound in a 90/10 weight ratio water/acetone mixture containing a small amount of a non-ionic surfactant. The resultant stock solution or dispersion was then diluted with a water-surfactant mixture to obtain the desired concentration of triorganotin compound while maintaining the surfactant concentration at 100 parts per million (ppm). Samples which proved difficult to emulsify were homogenzied using a colloid mill or tissue homogenizer.

2. Evaluation of Spray Formulations and Fungicides and Miticides

The test organisms employed were powdery bean mildew, apple scab, leaf spot of rice (helminthosporium) and the two-spotted spider mite. Triphenyltin hydroxide or tricyclohexyltin hydroxide was used as a control. These compounds are considered equivalent in performance to the corresponding oxides. The results of the evaluations are summarized in the following section.

The rating system employed to determine control of the organisms was based on a numerical scale wherein a rating of 10 indicated 100% control (no surviving organisms) and a rating of 0 indicated no control, i.e., a plant heavily infested with the organism. The control rating employed for bean mildew, leaf spot of rice and apple scab are a function of the fraction of total leaf area which remains unaffected by these fungi.

A. Powdery Bean Mildew

Tender green bean plants with fully expanded primary leaves are inoculated with spores of the powdery mildew fungus (Erysiphe polygoni) 48 hours prior to the application of dicyclohexylphenyltin hydroxide. The tin compound is applied at the concentrations indicated in the following table by placing the plants on a revolving turntable and spraying them with a formulation containing the triorganotin compound until the spray runs off the upper surface of the leaves. When the spray deposit dries, the plants are placed in a greenhouse for 14 days. The amount of mildew on the primary leaves is rated after the plants have remained in the greenhouse for 7 and 14 days. Untreated plants exhibit a rating of 1.0 or less after 7 days in the greenhouse. The formulations tested contained 100 or 20 parts per million (ppm) of either dicyclohexylphenyltin hydroxide or triphenyltin hydroxide.

B. Apple Scab

Frozen apple leaves which were infested with conidia spores were soaked in cool water for about 30 minutes, following which the liquid phase was filtered through a single layer of cheesecloth. A number of apple seedlings in the fifth leaf stage were sprayed with the water containing the dispersed conidia spores. The seedlings were stored in a high humidity environment [relative humidity (R.H.) = 100%] at ambient temperature for two days, after which they were stored at a temperature of 24±3° C. for 7 days, then in the high humidity environment for between 1 and 2 days, and finally at 24±3° C. for 10 to 15 days, during which time the infested leaves were harvested. The leaves were extracted with cool water to prepare a suspension which when viewed under a microscope at 100 X magnification exhibited a field containing not less than 20 conidia spores.

The plants to be tested were sprayed to the point of saturation with a liquid formulation prepared as previously described and containing dicyclohexylphenyltin hydroxide. After the liquid had evaporated the leaves were sprayed with the aforementioned suspension of conidia spores. The plants were then placed in a high humidity (100% R.H.) environment at ambient temperature for two days, after which they were stored under conditions of ambient humidity and a temperature of 24±3° C. until evidence of apple scab was observed on the untreated control plants as indicated by brownish lesions on the leaves. The results of the test are summarized below.

| Concentration of Organotin Compound (ppm) | Control Rating |
| --- | --- |
| 250 | 9.9 |
| 50 | 9.9 |
| 12.5 | 9.1 |

No evidence of phytoxicity was observed on the treated plants.

C. Two-spotted Spider Mite

Bean plants were sprayed with formulations containing a dispersed form of dicyclohexylphenyltin hydroxide at concentrations of 50 and 200 ppm. The particle size of the dispersion was between 50 and 100 microns. Between one and three days following the spraying a number of nymph stage and adult spider mites were transferred onto the upper surface of the plant leaves. The plants remained undisturbed at 24±3° C. for between 12 and 14 days following exposure to the mites, at which time the percentages of dead nymphs and adult mites were observed and the results recorded as

| | | CONTROL RATING | |
| --- | --- | --- | --- |
| CONCENTRATION (ppm) | DAYS FOLLOWING INITIAL SPRAYING | DICYCLYHEXYL-PHENYLTIN HYDROXIDE | TRIPHENYLTIN HYDROXIDE |
| 100 | 7 | 10.0 | 9.7 |
|  | 14 | 10.0 | 2.0 |
| 20 | 7 | 8.5 | 5.0 |
|  | 14 | 5.0 | 0.0 |

None of the foregoing formulations damaged the plants to any significant extent.

the initial control test. The long-term control of the triorganotin compound was evaluated by placing a new supply of adult and nymph stage mites onto the bean plant leaves following the initial observations. No additional triorganotin compound was applied. The percentages of dead nymph and adult mites were again observed between 21 and 30 days following the initial application of the mites, and the results recorded as the residual control test.

| CONCENTRATION OF TIN COMPOUND IN SPRAY (ppm) | INITIAL CONTROL | RESIDUAL CONTROL |
|---|---|---|
| 200 | 10 (A); 10 (N) | 10 (A); 9.9 (N) |
| 50 | 10 (A); 9.9 (N) | 10 (A); 9.9 (N) |

A = adult mites; N = nymph stage mites

D. Brown Spot (Helminthosporium) of Rice

Rice plants were sprayed with a formulation containing 200 parts per million of dicyclohexylphenyltin hydroxide, triphenyltin hydroxide or tricyclohexyltin hydroxide. Three days after being sprayed the plants were innoculated with a suspension of Helminthosporium spores, placed in an incubation chamber for 24 hours, then removed from the chamber and allowed to remain under ambient conditions until such time as lesions developed on the leaves of untreated control plants. All three formulations tested exhibited control ratings of between 8 and 9. The plants treated with tricyclohexyltin hydroxide and triphenyltin hydroxide were visibly damaged. No such phytotoxic effects were observed on the plants treated with dicyclohexylphenyltin hydroxide.

3. Acute Oral Toxicity of Dicyclohexylphenyltin Hydroxide Relative to bis(triphenyltin) Oxide Suspensions of dicyclohexylphenyltin hydroxide in corn oil were administered directly into the stomach of male albino rats (Charles River strain) using a hypodermic syringe equipped with a ball-tipped intubating needle. Food was withheld during the 16-hour period immediately prior to administration of the organotin compound. Following intubation the rats were caged individually and observed for 14 days. Any deaths which occurred during this period were recorded. A total of 12 rats, divided into groups of 2, were tested and each group received a different dosage of the triorganotin compound. The dosages (expressed in mg. of compound per kg. of body weight of the rat), were 118.5, 177.8, 266.7, 400.0, 600.0 and 900.0. The compound was administered as a 10% suspension in corn oil (10 g. of compound per 100 c.c. of corn oil) at the 118.7 and 177.8 mg./kg. levels. At other levels a 25% suspension was employed.

The acute oral median lethal dose ($LD_{50}$) for bis(triphenyltin)oxide is reported by M. J. Marks, Jr. in a thesis presented to the Graduate School of Duquesne University. The experimental conditions employed for the determination were similar to those described for dicyclohexylphenyltin hydroxide, the differences being the particular strain of albino rat (Sprague-Dawley), a fasting period of 24 rather than 16 hours prior to intubation and the use of a 1% aqueous acacia suspension in place of corn oil as the vehicle for administering the compound.

| DOSE OF TOXICANT (mg./kg. body weight) | No.Dead/No.Dosed | % Dead |
|---|---|---|
| Dicyclohexylphenyltin hydroxide | | |
| 118.5 | 0/2 | 0 |
| 177.8 | 0/2 | 0 |
| 266.7 | 1/2 | 50 |
| 400.0 | 1/2 | 50 |
| 600.0 | 2/2 | 100 |
| 900.0 | 2/2 | 100 |
| Bis(Triphenyltin) oxide | | |
| 100 | 1/6 | 16.7 |
| 150 | 3/6 | 50 |
| 225 | 4/6 | 66.7 |
| 337.5 | 4/6 | 66.7 |
| 506.25 | 4/6 | 66.7 |

For both of the foregoing compounds the acute oral median lethal dose ($LD_{50}$) was calculated using the method of Weil (Tables for Convenient Calculation of Median Effective Dose and Instructions in Their Use, Biometrics, 8; 249–263; Sept., 1952). The $LD_{50}$ values for dicyclohexylphenyltin hydroxide and bis(triphenyltin)oxide were 326.7 mg./kg. and 171 mg./kg., respectively. The present dicyclohexylphenyltin compound is therefore nearly half as toxic as the triphenyltin compound. Since a triorganotin hydroxide and the corresponding bis(triorganotin)oxide differ only by the presence of a mole of water in every two moles of the hydroxide, i.e., $2 R_3SnOH \rightarrow (R_3Sn)_2O + H_2O$, one would expect the two compounds to exhibit similar chemical properties, including toxicity toward plants and animals.

Although dicyclohexylphenyltin hydroxide was the only compound employed to determine biological activity, other dicyclohexylphenyltin derivatives, including fluorides, chlorides, bromides, carboxylates, mercaptides, alkoxides, phenoxides, sulfides and sulfates would be at least equally efficacious in combating fungi and mites. It has been shown by recognized experts that the anionic radical of the present triorganotin compounds, represented by X or Y in the foregoing generic formulae, have little, if any, effect on the level of biological activity exhibited by the compound unless the anion itself possesses significant biological activity. This disclosure appears in a paper by G. J. M. VanDerKerk et al [Journal of Applied Chemistry, 4, 314–319 (1954)].

What is claimed is:
1. A method for killing mites by contacting the mites on their plant habitat with a composition comprising a liquid or solid inert carrier and a miticidally effective but non-phytotoxic amount of a dicyclohexylphenyltin compound of the general formula

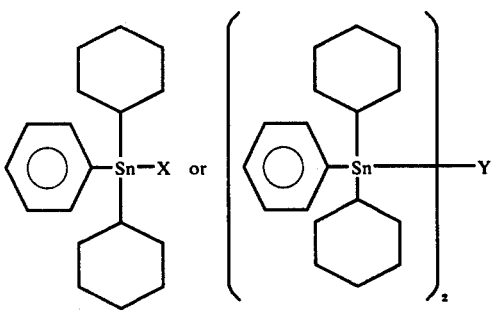

wherein X represents a monovalent radical selected from the group consisting of chlorine, bromine, fluorine, hydroxyl, carboxylate, phenoxy, alkoxy ($-OR^1$) and mercaptide ($-SR^2$), wherein $R^1$ represents an alkyl radical containing between 1 and 12 carbon atoms, inclusive, $R^2$ represents a radical selected from the same group as $R^1$ or a phenyl radical and Y is selected from the group consisting of oxygen, sulfur and sulfate radicals.

* * * * *